(12) United States Patent
Reaney et al.

(10) Patent No.: US 6,822,104 B2
(45) Date of Patent: Nov. 23, 2004

(54) METHOD FOR COMMERCIAL PREPARATION OF PREFERRED ISOMERIC FORMS OF ESTER FREE CONJUGATED FATTY ACIDS WITH SOLVENTS SYSTEMS CONTAINING POLYETHER ALCOHOL SOLVENTS

(75) Inventors: Martin J. T. Reaney, Saskatoon (CA); Sean Jones, Campbell River (CA); Neil D. Westcott, Saskatoon (CA)

(73) Assignee: Her Majesty the Queen in right of Canada, as represented by the Minister of Agriculture, Ottawa (CA)

( * ) Notice: Subject to any disclaimer, the term of this patent is extended or adjusted under 35 U.S.C. 154(b) by 22 days.

(21) Appl. No.: 10/220,143
(22) PCT Filed: Jan. 11, 2001
(86) PCT No.: PCT/CA01/00021
§ 371 (c)(1),
(2), (4) Date: Dec. 17, 2002
(87) PCT Pub. No.: WO01/51597
PCT Pub. Date: Jul. 19, 2001

(65) Prior Publication Data
US 2004/0015001 A1 Jan. 22, 2004

Related U.S. Application Data
(60) Provisional application No. 60/175,631, filed on Jan. 12, 2000.

(51) Int. Cl.$^7$ ............................................. C07C 51/347
(52) U.S. Cl. ........................................................ 554/126
(58) Field of Search ......................................... 554/126

(56) References Cited
U.S. PATENT DOCUMENTS
2,343,644 A * 3/1944 Cawley ....................... 554/34

* cited by examiner

Primary Examiner—Deborah D Carr
(74) Attorney, Agent, or Firm—Dowell & Dowell

(57) ABSTRACT

Methods for sequential saponification and quantitative isomerization of glyceride oils containing interrupted double bond systems, with alkali in a polyether alcohol solvent to yield soaps with conjugated double bond systems are disclosed. The novel properties of the polyether alcohols allow the removal of water added with the alkali by boiling. The preferred embodiment uses a vegetable oil rich in linoleic acid such as sunflower or safflower oil, potassium hydroxide, phosphoric acid to neutralize the soaps. The reaction forms equal quantities of 9Z,11E-octadecadienoic acid and 10E,12Z-octadecadienoic acids.

17 Claims, 4 Drawing Sheets

METHOD FOR COMMERCIAL PREPARATION OF PREFERRED ISOMERIC FORMS OF ESTER FREE CONJUGATED FATTY ACIDS WITH SOLVENTS SYSTEMS CONTAINING POLYETHER ALCOHOL SOLVENTS

BACKGROUND OF THE INVENTION AND CROSS-REFERENCE TO RELATED APPLICATION

This application claims the benefit of Provisional Application No. 60/175,631 filed Jan. 12, 2000.

This application is related to U.S. patent application Ser. No. 09/451,710 filed Dec. 1, 1999 by Martin J. T. Reaney et al, the disclosure of which is incorporated herein by reference.

FIELD OF INVENTION

This invention relates to an improved process for preparation of conjugated fatty acids from materials rich in fatty acids containing interrupted diene, triene and polyene systems. In a preferred embodiment the reaction produces approximately equal amounts of the conjugated linoleic acid isomers 9Z,11E-octadecadienoic acid and 10E,12Z-octadecadienoic acid from linoleic acid. The reaction is unique in that the reaction proceeds rapidly at temperatures as low as 90° C. The process by-product stream is usable directly as a fertilizer that limits waste disposal costs.

Interrupted dienes moieties of fatty acids and esters thereof may be converted to conjugated dienes, and higher polymers may also be conjugated. For examples, literature reports the synthesis of conjugated forms of linoleic acid, linolenic acid and arachidonic acid using alkali catalysts. Of the conjugated fatty acids that have been prepared, conjugated forms of linoleic acid are the most investigated. Conjugated linoleic acid or CLA is the trivial name given to a series of eighteen carbon diene fatty acids with conjugated double bonds. Applications of, and uses for, conjugated linoleic acids vary from treatment of medical conditions such as anorexia (U.S. Pat. No. 5,430,066) and low immunity (U.S. Pat. No. 5,674,901) to applications in the field of dietetics, where CLA has been reported to reduce body fat (U.S. Pat. No. 5,554,646) and to inclusion in cosmetic formulae (U.S. Pat. No. 4,393,043).

Conjugated fatty acids, specifically CLA shows similar activity in veterinary applications. In addition, CLA has proven effective in reducing valgus and varus deformity in poultry (U.S. Pat. No. 5,760,083), and attenuating allergic responses (U.S. Pat. No. 5,585,400). CLA has also been reported to increase feed conversion efficiency in animals (U.S. Pat. No. 5,428,072). CLA-containing bait can reduce the fertility of scavenger bird species such as crows and magpies (U.S. Pat. No. 5,504,114).

Industrial applications for conjugated fatty acids also exist where they may be used as lubricant constituents (U.S. Pat. No. 4,376,711). Conjugation can be used as a means to chemically modify fatty acids, such as linoleic acid, so that they are readily reactive to Diels-Alder reagents (U.S. Pat. No. 5,053,534). In one method linoleic acid was separated from oleic acid by first conjugation then reaction with maleic anhydride followed by distillation (U.S. Pat. No. 5,194,640).

Conjugated fatty acids occur naturally in ruminant depot fats. The predominant form of conjugated fatty acid in ruminant fat is the 9Z,11E-octadecadienoic acid which is synthesized from linoleic acid in the rumen by microorganisms like *Butryvibrio fibrisolvens*. The level of CLA found in ruminant fat is in part a function of dietary 9Z,12Z-octadecadienoic acid and the level of CLA in ruminant milk and depot fat may be increased marginally by feeding linoleic acid (U.S. Pat. No. 5,770,247).

Conjugated fatty acids may also be prepared by any of several analytical and preparative methods. Pariza and Ha pasteurized a mixture of butter oil and whey protein at 85° C. for 5 minutes and noted elevated levels of CLA in the oil (U.S. Pat. No. 5,070,104). CLA produced by this mechanism is predominantly a mixture of 9Z,11E-octadecadienoic acid and 10E,12Z-octadecadienoic acid.

Conjugated fatty acids have also been produced by the reaction of soaps with strong alkali bases in molten soaps, alcohol, and ethylene glycol monomethyl ether (U.S. Pat. Nos. 2,389,260; 2,242,230 & 2,343,644). These reactions are inefficient, as they require the multiple steps of formation of the fatty acid followed by production of soap from the fatty acids, and subsequently increasing the temperature to isomerize the linoleic soap. The conjugated fatty acid product is generated by acidification with a strong acid (sulfuric or hydrochloric acid) and repeatedly washing the product with brine or $CaCl_2$. Iwata et al. (U.S. Pat. No. 5,986,116) overcame the need for an intermediate step of preparation of fatty acids by reacting oils directly with alkali catalyst in a solvent of propylene glycol under low water or anhydrous conditions. Reaney et al., in U.S. patent application Ser. No. 09/451/710, entitled "Commercial production of CLA", and Yurawecz, Mossaba, Kramer, Pariza and Nelson Eds. Advances in conjugated linoleic acid research, Vol. 1 pp.39–54 identified that conjugated fatty acid products prepared in the presence of glycol and other alcohols may transesterify with fatty esters and produce esters of the glycol. Such esters have been identified by Reaney et al. (unpublished data) in commercial products and in CLA prepared in propylene glycol by the method of U.S. Pat. No. 5,986,116. Esters of CLA containing fatty acids and propylene glycol have biological activity and therefore their presence in the CLA product is undesirable.

Conjugated fatty acids have been synthesized from fatty acids using $SO_2$ in the presence of a sub-stoichiometric amount of soap forming base (U.S. Pat. No. 4,381,264). The reaction of linoleic acid with this catalyst produced predominantly the all trans configuration of CLA.

Efficient synthesis of 9Z,11E-octadecadienoic from ricinoleic acid has been achieved (Russian Patent 2,021,252). This synthesis, although efficient, uses expensive elimination reagents such as 1,8-diazobicyclo-(5,4,0)-undecene. For most applications the cost of the elimination reagent increases the production cost beyond the level at which commercial production of CLA is economically viable.

Of these methods, alkali isomerization of soaps is the least expensive process for bulk preparation of conjugated fatty acids. However, the use of either monohydric or polyhydric alcohols in alkali isomerization of conjugated fatty acids can be problematic. Lower alcohols are readily removed from the conjugated product but they require the production facility be built to support the use of flammable solvents. Higher molecular weight alcohols and polyhydric alcohols are considerably more difficult to remove from the product and residual levels of these alcohols (e.g. ethylene glycol) may not be acceptable in the conjugated product.

Water may be used in place of alcohols in the conjugation of fatty acids by alkali isomerization of soaps (U.S. Pat. Nos. 2,350,583 and 4,164,505). When water is used for this reaction it is necessary to perform the reaction in a pressure vessel whether in a batch (U.S. Pat. No. 2,350,583) or continuous mode of operation (U.S. Pat. No. 4,164,505). The process for synthesis of conjugated fatty acids from soaps dissolved in water still requires a complex series of reaction steps. Bradley and Richardson (Industrial and Engineering Chemistry February 1942 vol. 34 no.2 237–242) were able to produce conjugated fatty acids directly from soybean triglycerides by mixing sodium hydroxide, water and oil in a pressure vessel. Their method eliminated the need to synthesize fatty acids and then form soaps prior to the isomerization reaction. However, they reported that they were able to produce oil with up to 40 percent CLA. Quantitative conversion of the linoleic acid in soybean oil to CLA would have produced a fatty acid mixture with approximately 54 percent CLA.

Commercial conjugated linoleic acid often contains a mixture of positional isomers that may include 8E,10Z-octadecadienoic acid, 9Z,11E-octadecadienoic acid, 10E,12Z-octadecadienoic acid, and 11Z,13E-octadecadienoic acid (Christie, W. W., G. Dobson, and F. D. Gunstone, (1997) Isomers in commercial samples of conjugated linoleic acid. J. Am. Oil Chem. Soc. 74,11,1231).

The present invention describes a method of production of conjugated fatty acids using a polyether alcohol, such as polyethylene glycol alone or with a co-solvent as a reaction medium and vegetable oil, a fatty acid or ester thereof containing one or more interrupted diene moieties. In a preferred embodiment the reaction products of linoleic acid in polyether glycol containing solvent are primarily 9Z,11E-octadecadienoic acid and 10E,12Z-octadecadienoic acid in equal amounts. The reaction product is readily released by acidification.

SUMMARY OF THE INVENTION

In the present invention the quantitative production of conjugated fatty acids from fatty acids and esters containing interrupted dienes or higher polymers is achieved by heating the oil in a polyether alcohol with an alkali base. As it is normal for small amounts of water to be present in the reaction materials this water may either be boiled from the reaction mixture by addition of heat or reaction must be performed in a pressurized vessel; thereafter, the reaction mixture is neutralized by a strong acid, with solutions of H3PO4 being preferred. Surprisingly. when polyethylene glycol (PEG), and other polyether alcohols, are used as a solvent, the boiling reaction mixture does not foam uncontrollably. Surprisingly, the PEG solvent allows the reaction to proceed rapidly at temperatures as low as 90° C. The selection of $H_3PO_4$ as the acid and KOH as the base allow the resultant salt solution to be disposed of in surface applications as a liquid or solid fertilizer. The reaction minimizes the production of undesirable isomers.

Thus, by one aspect of the invention there is provided a process for producing a preferred isomeric mix of a conjugated linoleic acid-rich fatty acid mixture comprising reacting a linoleic acid-rich oil with a base in the presence of a catalytic amount of said base, in a polyether alcohol solvent containing medium, at a temperature above 90° C., and separating said conjugated linoleic acid-rich fatty acid mixture from said solvent by the addition of acid. In a preferred embodiment, 300 MW polyethylene glycol is the preferred polyether alcohol.

DETAILED DESCRIPTION OF THE INVENTION

Figure 1:
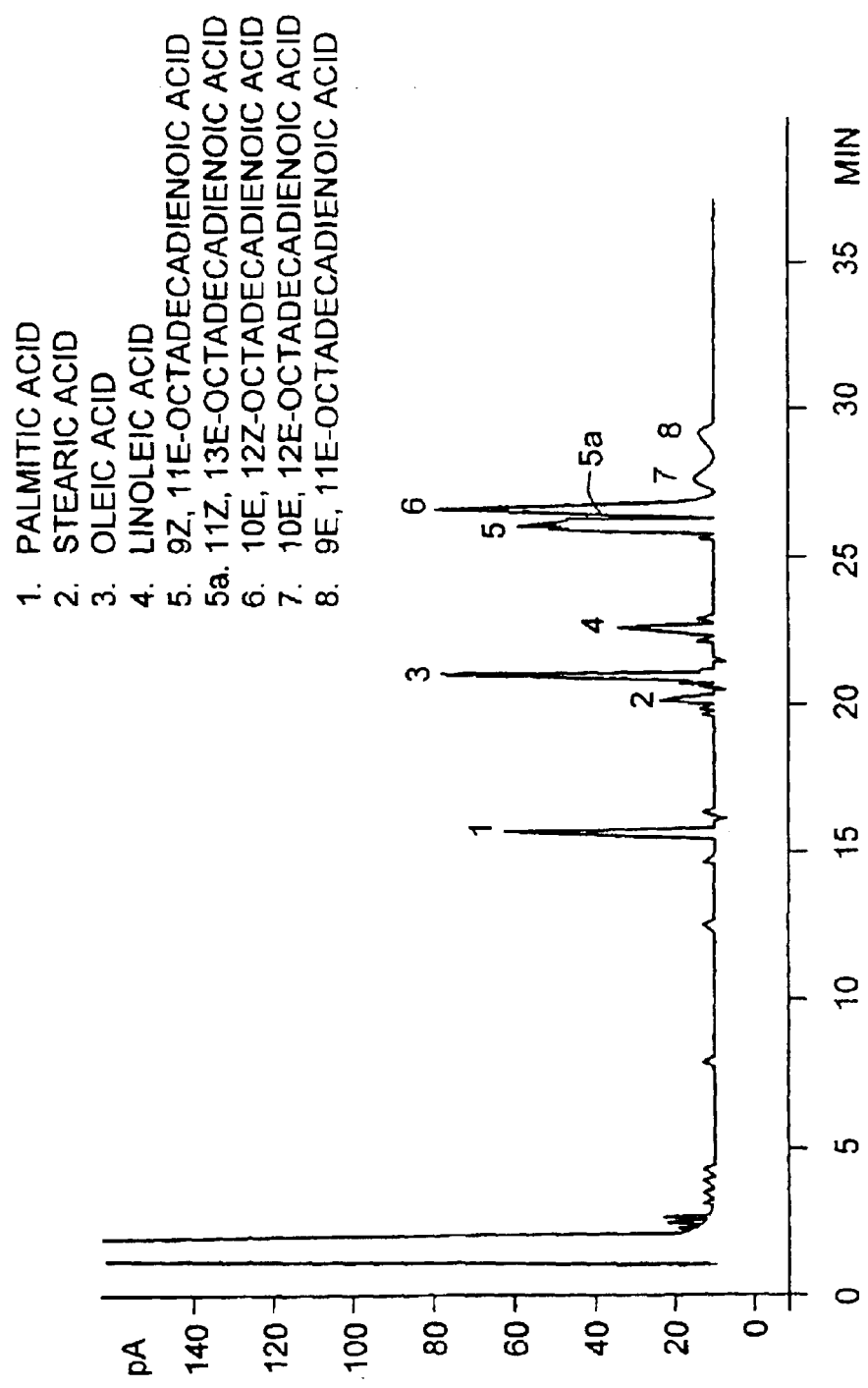
FIG. 1 is the gas liquid chromatogram of CLA prepared in water at 210° C. for 4 h.

The disclosed process quantitatively converts interrupted diene moieties or higher interrupted polymers occurring in vegetable oils, fatty acid and esters of fatty acids to conjugated dienes or polymers with conjugated double bond moieties respectively. The process involves blending said fatty acid or ester thereof with 1–6 moles of base, part of which acts as a reactant and part of which acts as a catalyst, dissolved in a polyether alcohol and 1 to 100 moles of water per mole of hydrolysable acyl groups. The vegetable oil, fatty acids and esters may include cottonseed, cucumber, grape seed, corn, safflower, soybean, sunflower or walnut oil or any other oil, wax or ester that is rich in interrupted diene moieties or borage oil, flax oil or any other oil, wax or ester that is rich in interrupted polyene moieties. The reaction will proceed if about 1 mole of a base such as sodium metal, sodium hydroxide, sodium alkoxylate, sodium carbonate, sodium bicarbonate, potassium metal, potassium hydroxide, potassium carbonate, potassium bicarbonate or potassium alkoxylate is used as reactant and up to 5 moles are used as the catalyst. The least expensive alkali that does not represent a disposal problem is potassium hydroxide. Furthermore, metallic alkali produces explosive hydrogen gas when added to water and metal alkoxylates are flammable. These factors support the use of potassium hydroxide as the preferred catalyst/reactant. The reaction proceeds at temperatures above 90° C. and accelerates with increases in temperature. The comparatively low reaction temperature achieved in polyethylene glycol is surprising as the reaction in a solvent containing ethylene glycol, the parent molecule, is 20 fold slower under the same conditions. We have found that the polyether alcohols are superior solvents to glycols. It is surprising that the conversion of vegetable oil to CLA may be performed in as little as 1 part of polyether alcohol solvent per 2 parts of interrupted fatty acid or ester thereof. Preferred embodiments involve performing the reaction above 130° C. It is a unique characteristic of this reaction that water in the reaction boils easily without foaming and it is not necessary to confine the reaction in a sealed pressure vessel.

The reaction proceeds very rapidly at temperatures above 130° C. and is sensitive to small changes in temperature. The reaction vessel used for the process must have a homogeneous temperature or the reaction will not proceed uniformly. Homogeneous temperature is achieved by stirring or turbulent flow conditions. In a preferred embodiment the reaction mixture is prepared with a sub-stoichiometric level of KOH and heated to the reaction temperature. The reactor is then charged with additional catalyst to begin the reaction. Using this method the reaction starts in the time required adding the catalyst. The reaction is terminated either through addition of acid or through the rapid cooling of the reaction mixture to prevent the further formation of positional isomers.

After the reaction is complete the mixture is cooled to 90–100° C. for separation of the reaction by-products. Acid is added to the reaction mixture to hydrolyze the soaps in the reactor. It is preferred to bring the pH of the contents of the reactor to pH 4 or less through the addition of either a mineral or organic acid. Acids that may be used include, but are not limited to, hydrochloric acid, sulfuric acid, phosphoric acid, carbonic and citric acid, it is found that the use of sulfuric and hydrochloric acid is problematic in that these strong acids may react chemically with the conjugated fatty acid during separation. The preferred embodiment of this invention involves the use of phosphoric acid or citric acid to hydrolyze the soaps. When phosphoric acid is used the waste solution can be neutralized and used as a surface applied fertilizer and there are no disposal costs for discarding this product.

Poly ethers have some solubility in the fatty acid phase. We have found that polyethylene glycol 300 (PEG) accumulated to a concentration of between 1 and 7 percent in the fatty acid phase during separation. This relatively high concentration of polyether alcohol could not be effectively removed from the fatty acids by water washing or washing with brine. However, we have discovered that the polyether alcohol could be removed from the fatty acid layer by washing the fatty acids with 70 percent aqueous phosphoric acid at between 85 and 110° C. We found that the emulsion breaking properties and phase partitioning properties of polyether alcohol molecules of widely different molecular sizes (PEG 300 and PEG 8,000, having molecular weights of 300 g/mole and 8000 g/mole respectively) to be similar.

Figure 2:
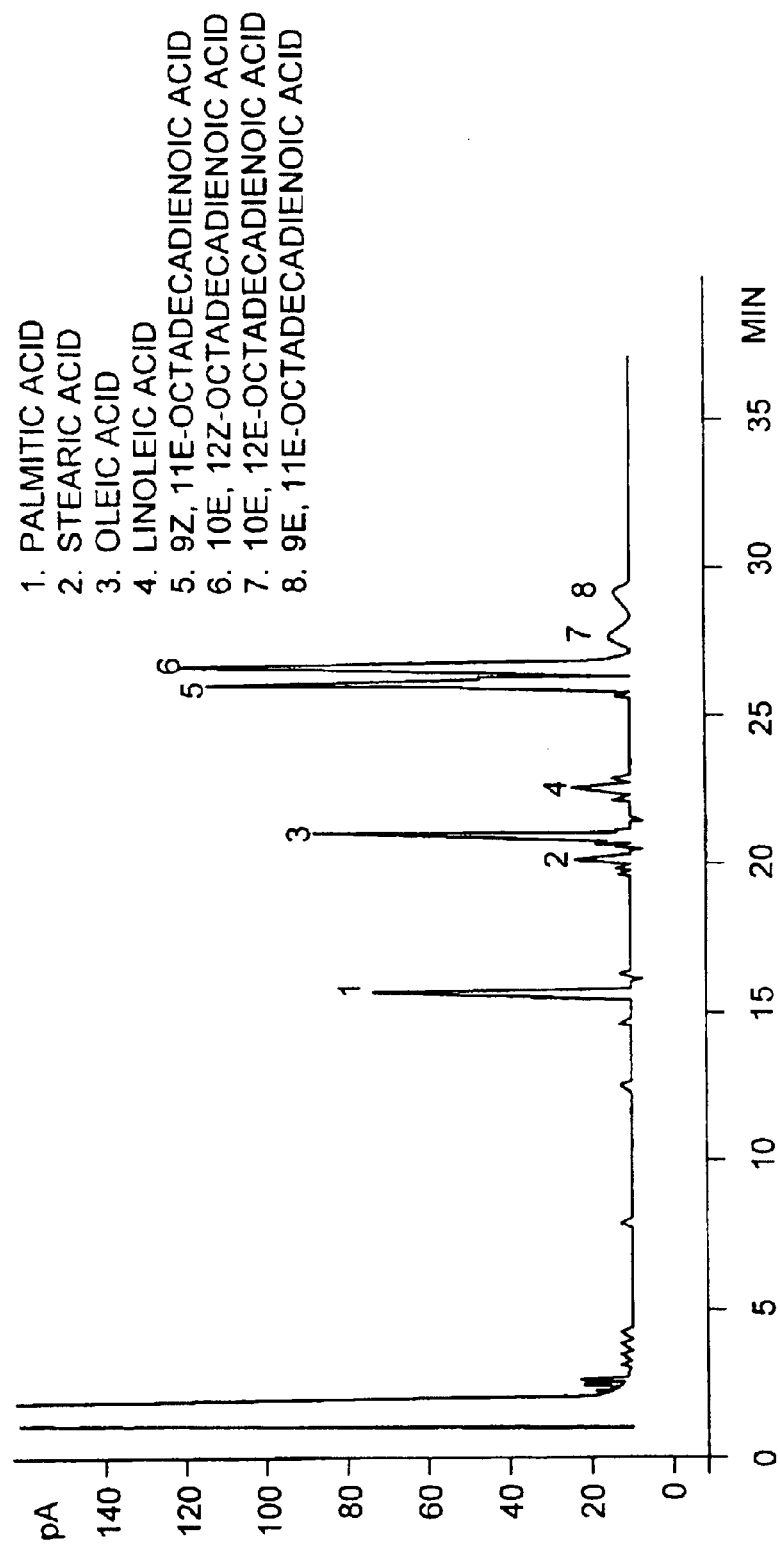
FIG. 2 is the gas liquid chromatogram of CLA prepared in PEG at 130° C. for 4 h.

Reaction progress was determined by gas liquid chromatography. FIG. 1 is the chromatogram of the product of reaction of sunflower with KOH in water and FIG. 2 is a chromatogram of the reaction of sunflower oil with KOH in PEG. As may be concluded from FIGS. 1 and 2, the reaction in water produces different isomers than the reaction in PEG. The reaction in PEG produces primarily the preferred 9Z,11E-octadecadienoic acid and 10E,12Z-octadecadienoic acid isomeric mixture.

Figure 3:
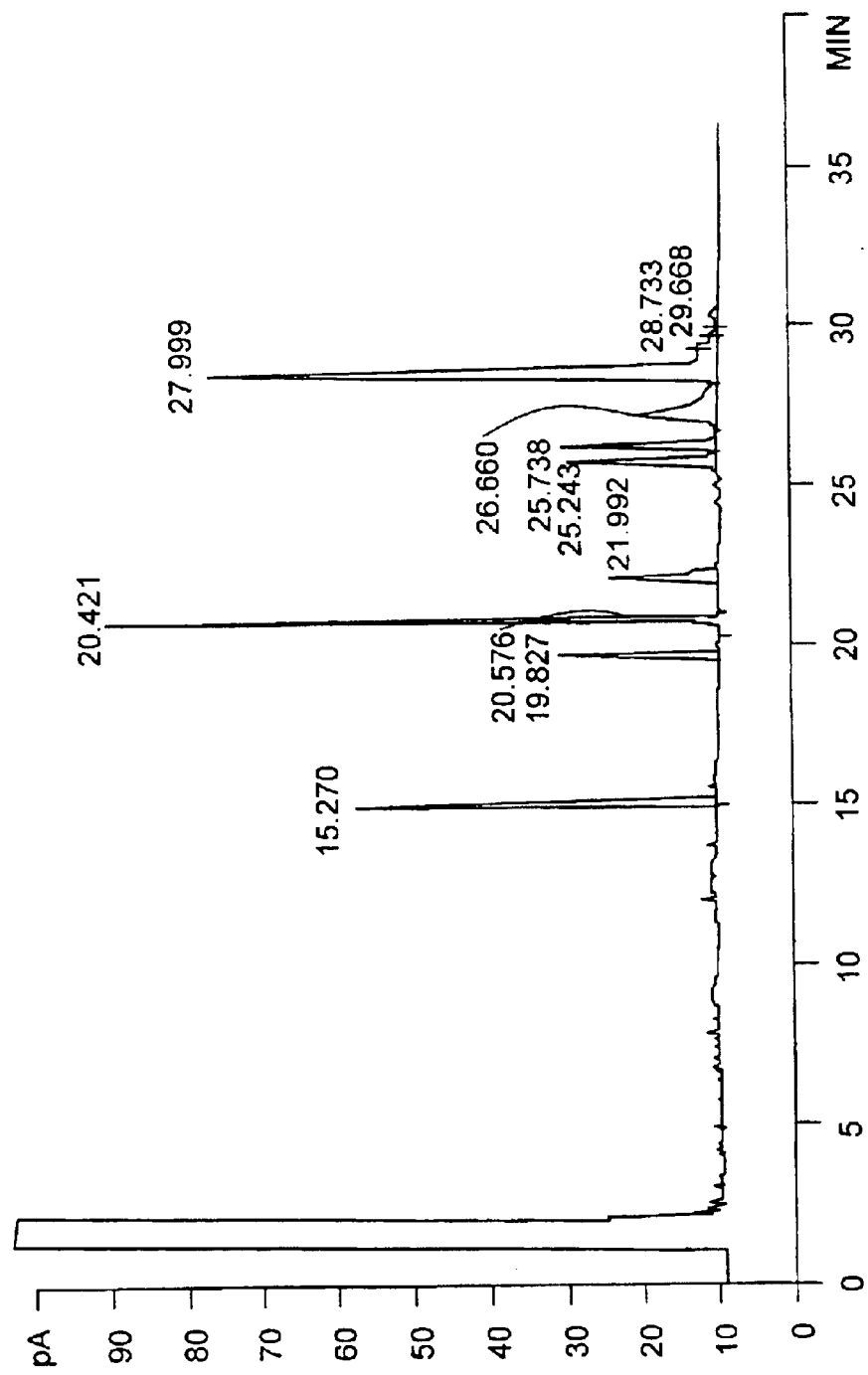
FIG. 3 is the gas liquid chromatogram of conjugated fatty acids prepared by treating flax oil in PEG at 130° C. for 4 h.
Figure 4:
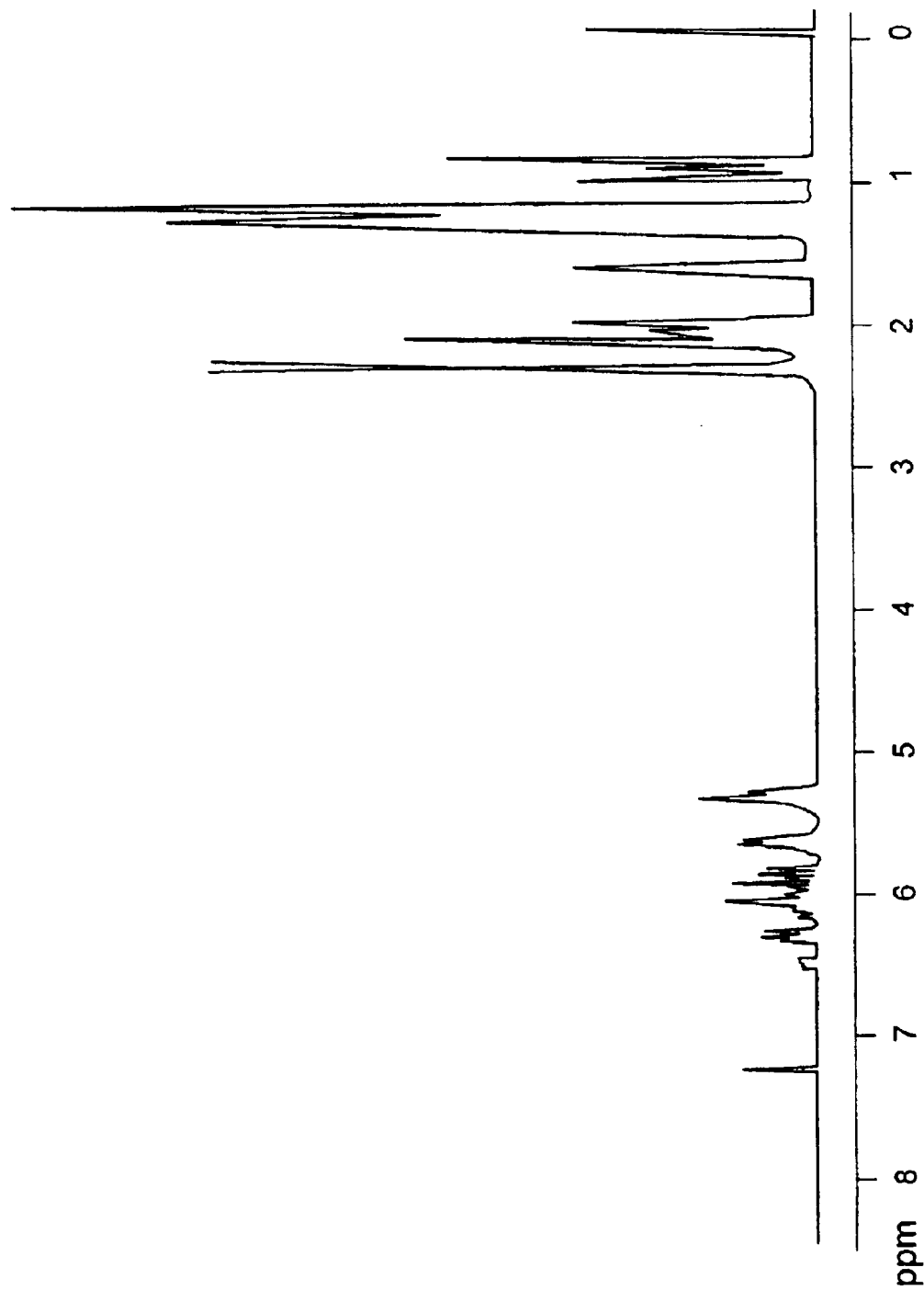
FIG. 4 is the 1H nuclear magnetic resonance spectrum of the conjugated fatty acids prepared by treating flax oil and KOH in PEG at 130° C. for 4 h.

From examination of FIG. 3 it is apparent that the signal normally associated with the methylene group between the two olefinic groups that should occur near 2.6 ppm is absent. It is also apparent that signals associated with conjugated diene systems in the 5.3 to 6.3 ppm region are now present. The absence of one signal with the concomitant appearance of the other signal is evidence that conjugation has been achieved. FIG. 4 indicates that there are the two expected peaks associated with conjugated linoleic acid, similar to FIG. 2, and a major apparent single peak at 28.3 minutes representing the conjugated linolenic acids.

EXAMPLES

Example 1
Sequential Hydrolysis and Isomerization of One Part Safflower Oil to CLA in One Part PEG 300.

To 600 g of PEG 300 were added commercial safflower oil (590 g) and aqueous KOH (45% w/w, 299 mL). The resulting reaction mixture was heated at 140° C. for 2 hours in a two liter beaker with vigorous agitation. During heating vigorous boiling occurred, as water was lost from the system. After cooling to 100° C., the reaction mixture was acidified with $H_3PO_4$ (85%, 222 ml).

The resulting mixture was heated for 0.5 h at 95° C. After standing for 0.5 hours at 95° C., the top CLA layer was removed, washed with $H_3PO_4$ (60%, 222 mL) at 95° C. for 30 minutes to remove excess PEG and water. The dried CLA layer was removed. The CLA product contained less than 0.1% water and less than 0.0125% PEG as determined by the method of Muir et al. (Muir, A., A. Aubin and M. J. T. Reaney 1998, "Determination of polyethylene glycol (PEG 300) in long chain free fatty acid mixtures by reverse phase high performance liquid chromatography", Journal of Chromatography A 810:241–244). The quantitative conversion of linoleic acid to CLA was confirmed by gas chromatography as described above. Under these reaction conditions most of the linoleic acid had reacted to form conjugated linoleic acids. Of the 74.2% linoleic acid in the starting material a total of 6.2% remained unreacted in the final product. Complete conversion of linoleic acid was achieved by longer reaction times not shown here.

TABLE 1

Fatty acid composition of CLA containing lipids derived from safflower oil.

| Fatty acid | Ex 1 | Ex 2 | Ex 3 | Ex 4 | Ex 5 | Ex 6 |
|---|---|---|---|---|---|---|
| Palmitic acid | 7.66 | 7.21 | 7.41 | 7.32 | 7.15 | 7.57 |
| Stearic Acid | 2.43 | 2.40 | 2.41 | 2.40 | 2.32 | 2.36 |
| Oleic acid | 16.01 | 15.75 | 15.73 | 15.70 | 15.26 | 15.94 |
| Linoleic acid | 6.17 | 13.04 | 2.27 | 4.00 | 65.54 | 3.48 |
| 9Z,11E-octadecadienoic acid | 31.41 | 28.30 | 33.73 | 32.52 | 4.12 | 31.83 |
| 10E,12Z-octadecadienoic acid | 32.21 | 30.47 | 35.10 | 34.41 | 4.24 | 35.21 |
| 9E,11E-octadecadienoic acid | 1.88 | 1.73 | 1.95 | 2.04 | <0.5 | 2.13 |
| 10E,12E-octadecadienoic acid | 1.52 | 1.08 | 1.39 | 1.60 | <0.5 | 1.44 |

| | Ex 7 | Ex 8 | Ex 11 | Ex 12 |
|---|---|---|---|---|
| Palmitic acid | 7.41 | 7.54 | 7.21 | 7.02 |
| Stearic Acid | 2.36 | 2.49 | 2.59 | 2.57 |
| Oleic acid | 15.65 | 16.27 | 8.61 | 8.89 |
| Linoleic acid | 33.70 | 1.76 | 7.38 | 1.49 |
| 9Z,11E-octadecadienoic acid | 18.82 | 33.02 | 33.78 | 37.42 |
| 10E,12Z-octadecadienoic acid | 19.56 | 34.46 | 36.84 | 39.21 |
| 9E,11E-octadecadienoic acid | 1.34 | 2.09 | 2.37 | 2.11 |
| 10E,12E-octadecadienoic acid | 1.13 | 2.36 | 1.21 | 1.26 |

Example 2
Sequential Hydrolysis and Isomerization of Two Parts Safflower Oil to CLA in One Part of PEG 300.

All conditions were similar to example 1 except that 300 g of PEG 300 were added commercial safflower oil (590 g) and aqueous KOH (45% w/w, 299 mL). The conversion of linoleic acid to CLA was confirmed by gas chromatography as described above. Under these reaction conditions most of the linoleic acid had reacted to form conjugated linoleic acids. Of the 74.2% linoleic acid in the starting material a total of 13.0% remained unreacted in the final product. Complete conversion of linoleic acid was achieved by longer reaction times not shown here

Example 3
Sequential Hydrolysis and Isomerization of Safflower Oil to CLA in PEG 200.

All conditions were similar to example 1 except that PEG 200 (molecular weight 200 g/mole) was substituted for PEG 300. The conversion of linoleic acid to CLA was confirmed by gas chromatography as described above. Under these reaction conditions most of the linoleic acid had reacted to form conjugated linoleic acids. Of the 74.2% linoleic acid in the starting material a total of 2.3% remained unreacted in the final product. Conversion of linoleic acid of linoleic acid to CLA could be considered to be complete for commercial purposes.

Example 4
Sequential Hydrolysis and Isomerization of Safflower Oil to CLA in PEG 600.

All conditions were similar to example 1 except that PEG 600 was substituted for PEG 300. The conversion of linoleic acid to CLA was confirmed by gas chromatography as described above. Under these reaction conditions most of the linoleic acid had reacted to form conjugated linoleic acids. Of the 74.2% linoleic acid in the starting material a total of 4.0% remained unreacted in the final product. Complete conversion of linoleic acid was achieved by longer reaction times not shown here

Example 5
Sequential Hydrolysis and Isomerization of Safflower Oil to CLA in Propylene Glycol.

All conditions were similar to example 1 except that propylene glycol was substituted for PEG 300. The conversion of linoleic acid to CLA was confirmed by gas chromatography, as described above. Under these reaction conditions very little of the linoleic acid had reacted to form conjugated linoleic acids. Of the 74.2% linoleic acid in the starting material a total of 65.5% remained unreacted in the final product. This result shows that propylene glycol is an inferior reaction solvent to polyether alcohols.

Example 6
Sequential Hydrolysis and Isomerization of Safflower oil to CLA in PEG 300 in a Sealed Pressure Reactor.

To 300 g of PEG 300 were added commercial safflower oil (295 g) and aqueous KOH (45% w/w, 149.5 mL). The resulting reaction mixture was heated at 180° C. for 4 hours in a sealed high pressure reactor with vigorous agitation. During heating boiling could not occur as the reactor was sealed throughout the reaction. After cooling to 100° C., the reaction mixture was removed and placed in a 2000 mL beaker and acidified with $H_3PO_4$ (60%, 222 ml). The resulting mixture was heated for 0.5 h at 95° C. After standing for 0.5 hours at 95° C., the top CLA layer was removed, washed with $H_3PO_4$ (60%, 222 mL) at 95° C. for 30 minutes to remove excess PEG and water. The dried CLA layer was removed. The CLA product contained less than 0.1% water and less than 0.0125% PEG as determined by the method of Muir et al., 1998. The quantitative conversion of linoleic acid to CLA was confirmed by gas chromatography as described above.

Example 7
Sequential Hydrolysis and Isomerization of Safflower Oil to CLA in a Mixture of PEG 300 and Propylene Glycol.

All conditions were similar to example 1 except that a mixture of propylene glycol and PEG 300 (1:1, w:w) was substituted for PEG 300 alone. The conversion of over half of the linoleic acid to CLA was confirmed by gas chromatography as described above. Of the 74.2% linoleic acid in the starting material a total of 31.8% remained unreacted in the final product. Comparison of this result to example 5 shows that PEG 300 can readily accelerate the conversion of linoleic acid to CLA in other solvents.

Example 8
Refining CLA Enriched Fatty Acids

The fatty acids produced by all of the methods mentioned above have a straw yellow colour and contain some metal ions as determined by inductively coupled plasma spectrometry. The yellow colour detracts from marketability and the metal ions may cause the material to be unstable. One thousand grams of fatty acid produced as described in example 1 was heated under vacuum in an agitated sealed vessel at 70° C. and 10 grams of bleaching clay (Supreme 120 FF), was added. The mixture was continuously stirred and heated to 105° C., under vacuum, for 30 minutes. When the temperature of the mixture had decreased to 60° C., the vacuum was released. The mixture was then filtered through a Celite filter bed. The refining treatment had no effect on the fatty acid composition of the CLA containing product but improved the colour to a lighter yellow.

Example 9
Removal of PEG from CLA by Washing with Phosphoric Acid.

Polyethylene glycol 300 (5 g) was dissolved in 100 grams of CLA rich oil produced as described in example 1 and the sample was heated and stirred in 50 mL water at 100° C. for 15 min. The PEG 300 content of upper CLA phase was determined by the method of Muir et al. 1998 (supra). It was found that substantial amounts of PEG were detectable in the CLA phase. The experiment was repeated in a similar manner except that the water was replaced with 50 mL of phosphoric acid and the mixture was stirred at 110° C. for 15 min. After the latter treatment PEG was not detected in the upper CLA rich phase.

Example 10
Production of CLA in PEG 300 in a Continuous Reactor.

To 300 g of PEG 300 were added commercial safflower oil (295 g) and solid KOH (74 g). The resulting reaction mixture was heated at 120° C. for 20 minutes in a one-liter beaker with vigorous agitation. During heating boiling occurred, as a small amount of water was lost from the system. After cooling to 60° C., the reaction mixture was pumped through a heated tubular reactor. The reaction temperature was adjusted to either 170° C. or 180° C. and the rate of pumping was adjusted so that the reaction time was between 5 and 15 minutes. The conversion of linoleic acid to CLA was confirmed by gas chromatography as described above (results shown in table 2). Under these reaction conditions longer retention times and higher temperatures increased the total conversion. One skilled in the art of reactor design could develop a reactor to continuously convert linoleic acid dissolved in alkali solutions to conjugated linoleic acid.

TABLE 2

| Fatty Acids | Flow Rate (Temp° C.) | | | | | |
|---|---|---|---|---|---|---|
|  | 1.5 (170) | 1.0 (170) | 0.5 (170) | 1.5 (180) | 1.0 (180) | 0.5 (180) |
| Palmitic Acid | 6.74 | 6.73 | 6.81 | 7.06 | 6.93 | 6.76 |
| Stearic Acid | 2.48 | 2.47 | 2.49 | 2.49 | 2.51 | 2.50 |
| Oleic Acid | 8.13 | 8.17 | 8.30 | 8.29 | 8.28 | 8.30 |
| Linoleic Acid | 76.24 | 68.77 | 61.03 | 69.79 | 60.21 | 43.94 |
| 9Z,11E-octa-decadienoic acid | 3.11 | 6.41 | 9.97 | 6.02 | 10.26 | 17.42 |
| 10E,12Z-octa-decadienoic acid | 3.29 | 6.48 | 10.62 | 6.35 | 10.94 | 18.90 |
| 9E,11E-octa-decadienoic acid | <0.5 | 0.60 | 0.77 | <0.5 | 0.87 | 1.51 |
| 10E,12E-octa-decadienoic acid | <0.5 | <0.5 | <0.5 | <0.5 | <0.5 | 0.68 |

Example 11
Sequential Hydrolysis and Isomerization of Safflower Oil to CLA in Isopropyl-idene-rac-Glycerol.

All conditions were similar to example 1 except that 1,2-O-isopropyl-idene-rac-glycerol (a diether alcohol with a chemical structure that is very different from polyethylene glycol) was substituted for PEG 300 and the reaction temperature was elevated to 150° C. The quantitative conversion of linoleic acid to CLA was confirmed by gas chromatography as described above.

Example 12
Production of CLA Using a Linoleic Acid Source >80%

All conditions were similar to example 1 except that a >80% linoleic acid source was substituted for safflower oil. The quantitative conversion of linoleic acid to CLA was confirmed by gas chromatography as described above.

Example 13
Commercial Scale Conversion of Safflower Oil to CLA in PEG 300

To 340 kg of PEG 300 was added solid KOH (80 kg). The resulting mixture was heated at 130° C. for 2 hours in 1000 liter reaction vessel with vigorous agitation. To the heated PEG was added commercial safflower oil (335 kg) and the temperature was raised and maintain at 140° C. for 4 hours with vigorous agitation. After cooling to 110° C., the reaction mixture was acidified with $H_3PO_4$ (75%, 220 kg). The resulting mixture was agitated for 0.5 h at 110° C. After standing for 0.1 hours at 110° C., the bottom layer containing salts, glycerol, PEG, excess $H_3PO_4$ and other non-free fatty acid materials was removed. The CLA layer was washed with $H_3PO_4$ (75%, 110 kg) and the CLA layer was separated. The acid washing step was repeated one more time. The CLA was finally vacuumed dried and filtered. The quantitative conversion of linoleic acid to CLA was confirmed by gas chromatography as described above.

Example 14
Commercial Scale Conversion of Sunflower Free Fatty Acids to CLA in PEG 300

To 340 kg of PEG 300 was added solid KOH (80 kg). The resulting mixture was heated at 130° C. for 2 hours in 1000 liter reaction vessel with vigorous agitation. To the heated PEG was added sunflower free fatty acid (335 kg) and the temperature was raised and maintain at 130° C. for 4 hours with vigorous agitation. After cooling to 105° C., the reaction mixture was acidified with $H_3PO_4$ (75%, 220 kg). The resulting mixture was agitated for 0.5 h at 110° C. After standing for 0.1 hours at 110° C. the top CLA layer was removed, washed with $H_3PO_4$ (75%, 110 kg) at 105° C. for 30 minutes to remove excess PEG and water. The washing step was repeated one more time. The CLA was finally vacuumed dried and filtered. The quantitative conversion of linoleic acid to CLA was confirmed by gas chromatography as described above.

Example 15
Sequential Hydrolysis and Isomerization Flax Oil to Conjugated Triene Fatty Acids in PEG 300.

To 600 g of PEG 300 were added commercial flax oil (590 g) and solid KOH (150 g). The resulting reaction mixture was heated at 130° C. for 4 hours in a 2 liter beaker with vigorous agitation After cooling to 100° C., a 5 ml aliquot of the reaction mixture was removed, acidified with excess $H_3PO_4$ (75%, 20 ml) and stirred at 100° C. for 15 minutes. The layers were allowed to separate and a sample of the top layer was removed for analysis. FIG. 3 shows the gas chromatographic profile of the isomerized product. FIG. 4 show the 1H nuclear magnetic resonance spectrum of the conjugated fatty acids prepared by heating flax oil and KOH in PEG at 130° C. for 4 h.

What is claimed is:

1. A process for producing a conjugated fatty acid-rich mixture comprising:

reacting a fatty acid rich oil that contains some fatty acids with moieties selected from interrupted diene, triene and polyene with a base, in the presence of a catalytic amount of said base, in an medium containing a polyether glycol solvent at a temperature above 90° C., and separating said conjugated fatty acid-rich fatty acid mixture from said polyether alcohol solvent by the addition of acid.

2. A process as claimed in claim 1 wherein said medium also contains a co-solvent.

3. A process as claimed in claim 1, wherein said oil is a vegetable oil selected from the group consisting of cottonseed, cucumber, grapeseed, corn, safflower, soybean, sunflower, flax seed, borage and walnut oil.

4. A process as claimed in claim 1, wherein said base is selected from the group consisting of sodium metal, sodium hydroxide, sodium alkoxylate, sodium bicarbonate, sodium carbonate, potassium metal, potassium hydroxide, potassium bicarbonate, potassium carbonate and potassium alkoxylate.

5. A process as claimed in claim 1 including the step of cooling said reaction mixture to a temperature of between about 90° and about 100° before said separating step.

6. A process as claimed in claim 1 wherein a pH of said cooled reaction mixture is reduced to less than pH 4.

7. A process as claimed in claim 1, wherein said acid is selected from the group consisting of hydrochloric, sulfuric, phosphoric and citric acid.

8. A process as claimed in claim 1 wherein said temperature is in the range 130°–180° C.

9. A process as claimed in claim 1 wherein said temperature is about 140° C.

10. A process, as claimed in claim 1, wherein the polyether alcohol solvent is polyethylene glycol with a molecular weight of at least 200 g/mole.

11. A process as claimed in claim 1, wherein at least 55% of said conjugated fatty acid produced comprises 9Z, 11E-octadecadienoic acid and 10E, 12Z-octadecadienoic acid.

12. A process as claimed in claim 1, wherein the reaction produces similar amounts of 10E, 12Z-octadecadienoic acid and 9Z, 11E-octadecadienoic acid.

13. A process as claimed in claim 2, wherein the polyether alcohol includes water as a cosolvent.

14. A process as claimed in claim 2, wherein the polyether alcohol includes an alcohol as a cosolvent.

15. A process as claimed in claim 2, wherein the polyether alcohol includes propylene glycol as a cosolvent.

16. A process as claimed in claim 2, wherein the polyether alcohol includes glycerol as a cosolvent.

17. A process as claimed in claim 1, wherein the process is a continuous reaction.

* * * * *